(12) United States Patent
Smith et al.

(10) Patent No.: US 12,605,163 B2
(45) Date of Patent: Apr. 21, 2026

(54) HOOK AND LOOP FOR HEMOSTASIS CLIP RELEASE

(71) Applicants: BOSTON SCIENTIFIC MEDICAL DEVICE LIMITED, Galway (IE); BOSTON SCIENTIFIC SCIMED, INC., Maple Grove, MN (US)

(72) Inventors: Paul Smith, Smithfield, RI (US); Matthew Bradley Adams, Harvard, MA (US); Deepak Kumar Sharma, Muzaffarnagar (IN)

(73) Assignees: Boston Scientific Scimed, Inc., Maple Grove, MN (US); Boston Scientific Medical Device Limited, Galway (IE)

( * ) Notice: Subject to any disclaimer, the term of this patent is extended or adjusted under 35 U.S.C. 154(b) by 550 days.

(21) Appl. No.: 18/058,585

(22) Filed: Nov. 23, 2022

(65) Prior Publication Data

US 2023/0157699 A1     May 25, 2023

Related U.S. Application Data

(60) Provisional application No. 63/264,490, filed on Nov. 23, 2021.

(51) Int. Cl.
| | |
|---|---|
| *A61B 17/122* | (2006.01) |
| *A61B 17/128* | (2006.01) |
| *A61B 17/00* | (2006.01) |

(52) U.S. Cl.
CPC ........ *A61B 17/1227* (2013.01); *A61B 17/128* (2013.01); *A61B 2017/0034* (2013.01)

(58) Field of Classification Search
CPC ........ A61B 2017/0034; A61B 17/1227; A61B 17/128; A61B 17/1285
See application file for complete search history.

(56) References Cited

U.S. PATENT DOCUMENTS

| | | | |
|---|---|---|---|
| 6,273,903 B1 | 8/2001 | Wilk | |
| 11,013,518 B2 | 5/2021 | Zhong et al. | |
| 2002/0062130 A1 * | 5/2002 | Jugenheimer ...... A61B 17/1285 606/142 |

(Continued)

FOREIGN PATENT DOCUMENTS

| | | |
|---|---|---|
| CN | 110559038 | 12/2019 |
| JP | 2011120884 A | 6/2011 |
| WO | 03/053256 A1 | 7/2003 |

*Primary Examiner* — Brooke Labranche
*Assistant Examiner* — Zehra Jaffri
(74) *Attorney, Agent, or Firm* — Fay Kaplun & Marcin, LLP

(57) ABSTRACT

A system includes an adapter mounted over a distal end of an insertion device, a clip and a first extending member. The clip includes jaws movable between an insertion configuration, with the jaws separated and an initial deployed configuration with the jaws drawn together. The clip is biased toward the initial configuration. The first jaw includes a connection element and a first member releasably coupled to the first jaw connection element permits movement of the adapter relative to the clip while the first member remains coupled to the clip to enhance visual observation of the clip. The first member retracts the clip proximally over the adapter so that the clip is forced open as the clip is retracted over the adapter freeing the clip from tissue on which it had been clipped.

14 Claims, 5 Drawing Sheets

(56) References Cited

U.S. PATENT DOCUMENTS

| | | | |
|---|---|---|---|
| 2004/0147943 A1* | 7/2004 | Kobayashi | A61B 34/76 |
| | | | 606/158 |
| 2011/0224706 A1* | 9/2011 | Weitzner | A61B 17/1285 |
| | | | 606/157 |
| 2012/0053603 A1 | 3/2012 | Williamson, IV | |
| 2020/0397445 A1 | 12/2020 | Shikhman et al. | |

* cited by examiner

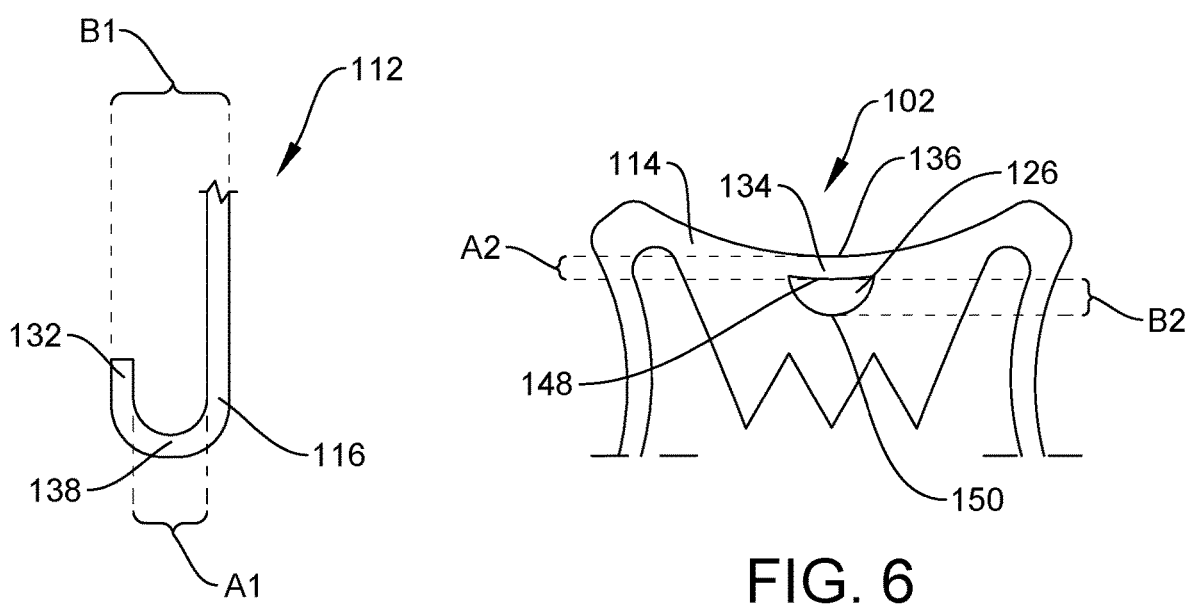
FIG. 5
FIG. 6
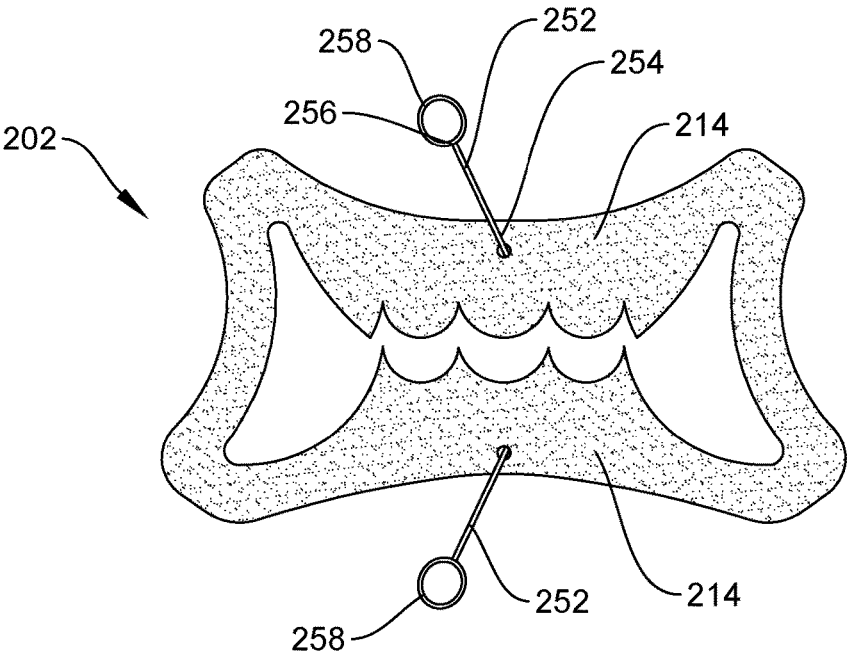
FIG. 7

HOOK AND LOOP FOR HEMOSTASIS CLIP RELEASE

PRIORITY CLAIM

The present disclosure claims priority to U.S. Provisional Patent Application Ser. No. 63/264,490 filed Nov. 23, 2021; the disclosure of which is incorporated herewith by reference.

FIELD

The present disclosure relates to endoscopic devices and, in particular, relates to endoscopic clipping devices for treating tissue along the gastrointestinal tract.

BACKGROUND

Physicians have become more willing to perform aggressive interventional and therapeutic endoscopic gastrointestinal (GI) procedures, which may increase the risk of perforating the wall of the GI tract or may require closure of the GI tract wall as part of the procedure. Such procedures may include, for example, the removal of large lesions, tunneling under the mucosal layer of the GI tract to treat issues below the mucosa, full thickness removal of tissue, treatment of issues involving organs outside the GI tract by passing through a wall of the GI tract, and endoscopic treatment/repair of post-surgical issues (e.g., post-surgical leaks, breakdown of surgical staple lines, and anastomotic leaks).

Currently, tissue may be treated via endoscopic closure devices including through-the scope clips or over-the-scope clips. Over-the-scope clips may be particularly useful for achieving closure of larger tissue defects. These endoscopic closure devices can save costs for the hospital as well as providing benefits for the patient. In some cases, however, current endoscopic closure devices may be difficult to use, time consuming to position, or insufficient for certain perforations, conditions and anatomies. For example, current over-the-scope clips may require launching of the clip from a position in which the clip itself is not visible to the operator. That is, prior to clipping the operator may view the target tissue to be clipped and, based on this visualization of the target tissue and an understanding of the positioning of the unseen clip relative to the field of view may determine that the distal end of the device and the clip are in a desired position relative to the target tissue. Based on the observation of the target tissue, the operator then deploys the clip without being able to see the clip itself until it is deployed. Once deployed, such current over-the scope clips are generally incapable of being repositioned.

SUMMARY

The present disclosure relates to a clipping system for treating tissue. The system includes an adapter extending longitudinally from a proximal end configured to be mounted over a distal end of an insertion device to a distal end; a clip; and a first extending member. The clip includes first and second jaws connected to one another so that the first and second jaws are movable between an insertion configuration, in which the first and second jaws are separated from one another to receive tissue therebetween and an initial deployed configuration in which the first and second jaws are drawn toward one another to grip tissue therebetween. The clip is biased toward the initial deployed configuration. The first jaw includes a first jaw connection element. The first extending member is configured to be releasably coupled to the clip. The first extending member extends from a proximal end accessible to a user at a proximal end of the insertion device to a first extending member connection device configured to releasably couple to the first jaw connection element. The first extending member is configured to permit movement of the adapter relative to the clip while the first extending member remains coupled to the clip to place the system in a review configuration in which the clip is physically spaced from the adapter to enhance visual observation of the clip. The first extending member is operable to retract the clip proximally over the adapter so that the clip is forced open as the clip is retracted over the adapter freeing the clip from tissue on which it had been clipped.

In an embodiment, the jaw connection element includes a slot extending through each of the jaws and wherein the first extending member connection device includes a hook, the slot being sized and shaped to releasably receive the hook.

In an embodiment, a width of the slot is smaller than a diameter of a curvature of the hook.

In an embodiment, a width the slot is larger than a width of the distal end of the first extending member so that the distal end of the first extending member is releasable from the first jaw connection element.

In an embodiment, the first jaw connection element includes a wire extending from the first jaw and wherein the first extending member connection device includes a hook-shaped curvature at the distal end of the first extending member, the wire including a loop configured to engage the hook-shaped curvature of the first extending member.

In an embodiment, a first end of the wire is attached to the first jaw and a second end of the wire includes the loop sized, shaped and configured to be hooked via the distal end of the first extending member.

In an embodiment, the wire is looped through a hole extending through the first jaw to form a closed loop configured to be hooked via the distal end of the first extending member.

In an embodiment, the wire extends from a first end to a second end, each of the first and second ends attached to a surface of the first jaw so that the wire defines a loop configured to be hooked via the hook-shaped curvature of the first extending member.

In an embodiment, the system further includes a second extending member releasably coupled to a second jaw connection element of the second jaw. The second extending member connection device includes a hook-shaped curvature at the distal end of the second extending member for engaging the second jaw connecting element.

The present disclosure also includes a clipping system for treating tissue. The system includes an endoscope extending longitudinally from a proximal end to a distal end; an adapter, a clip, and first and second extending members. The adapter extends longitudinally from a proximal end configured to be mounted over the distal end of the endoscope so that a channel of the adapter is aligned with a channel of the endoscope. The clip includes first and second jaws connected to one another so that the first and second jaws are movable between an insertion configuration, in which the first and second jaws are separated from one another to receive tissue therebetween and an initial deployed configuration in which the first and second jaws are drawn toward one another to grip tissue therebetween. The clip is biased toward the initial deployed configuration. The first jaw includes a first jaw connection element. The first and second extending members are configured to be releasably coupled to the clip and movably connected to the adapter. The first and second extending members extends from proximal ends accessible to a user at a proximal end of the endoscope. A distal end of the first extending member includes a first extending member connection device configured to be releasably connected to the first jaw connection element so that longitudinal movement of the first extending member relative to the endoscope moves the clip between the insertion configuration, the initial deployed configuration and a review configuration in which the clip is physically separated from the adapter to enhance visual observation of the clip.

In an embodiment, the first jaw connection element includes a slot extending therethrough and wherein the first extending member connection device includes a hook at a distal end of the first extending member, the slot defining an engaging section of the first jaw between the slot and an exterior edge of the first jaw, the engaging section configured to be received within the hook-shaped curvature of the first extending member.

In an embodiment, the first jaw includes a wire coupled thereto, the wire including a loop configured to engage the hook-shaped curvature of the first extending member.

In an embodiment, a first end of the wire is attached to the first jaw and a second end of the wire includes the loop that is sized, shaped and configured to be hooked via the distal end of the first extending member.

In an embodiment, the wire extends from a first end to a second end, each of the first and second ends being attached to a surface of the first jaw so that the wire defines a loop configured to be hooked via the hook-shaped curvature of the first extending member.

In addition, the present disclosure relates to a method for treating tissue. The method includes inserting a clip to a target area in a body lumen via an endoscope, the clip mounted over a distal end of the endoscope, via an adapter, in an insertion configuration in which jaws of the clip are separated from one another; applying a suction force through a working channel of the endoscope so that tissue is drawn into a channel of the adapter and between the jaws of the clip; moving the clip from the insertion configuration toward an initial deployed configuration by releasing tension along extending members coupled to the clip so that the jaws revert under a spring bias to a closed configuration in which the jaws move toward one another to grip tissue received therebetween, the extending members releasably coupled to the clip; and moving the endoscope relative to the clip while the extending members remain coupled to the clip to a review configuration in which a visualization of the clip via the endoscope is enhanced.

In an embodiment, when it is determined that the clip requires repositioning, moving the extending members proximally relative to the endoscope until the clip is drawn proximally over the adapter to the insertion configuration and repositioning the clip over the target area.

In an embodiment, the method further includes moving the extending members distally relative to the clip while in the review configuration, to disengage the extending members from the clip and release the clip to a final deployed configuration.

In an embodiment, the extending members are biased one of toward and away from one another so that, upon disengagement of the extending members from the clip, the endoscope and the extending members may be withdrawn proximally from the body.

In an embodiment, each of the extending members is independently released from the clip by moving the distal end of the endoscope laterally with respect to the clip so that each of the extending members is independently movable relative to the clip and proximally withdrawable therefrom.

BRIEF DESCRIPTION

FIG. 5 shows a side view of a distal portion of an extending member according to the system of FIG. 1;

FIG. 6 shows a partial plan view of the clip according to the system of FIG. 1;

FIG. 7 shows a plan view of a clip according to another exemplary embodiment of the present disclosure;

DETAILED DESCRIPTION

Figure 1:
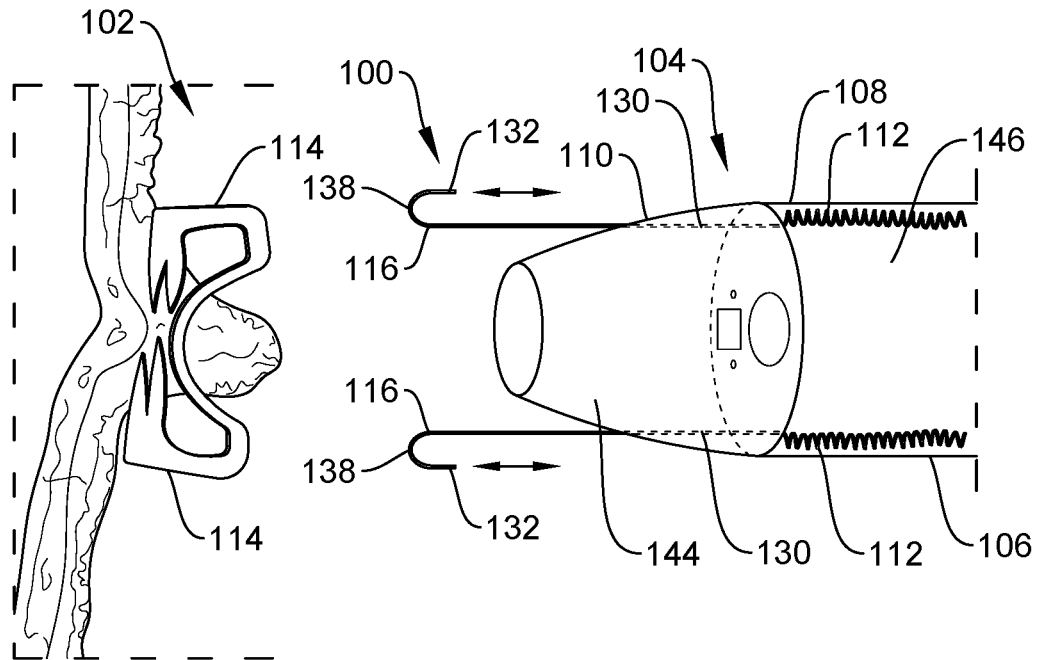
FIG. 1 shows a longitudinal side view of a system according to an exemplary embodiment of the present disclosure.

The present disclosure may be further understood with reference to the following description and the appended drawings, wherein like elements are referred to with the same reference numerals. The present disclosure relates to a clipping system and, in particular, relates to an over-the-scope endoscopic clipping system, in which an initial placement of a clip may be viewed and adjusted prior to a final deployment thereof. Exemplary embodiments of the present disclosure comprise a clip mountable over a distal end of an endoscope via an adapter and releasably coupled to extending members so that the clip may be moved between an insertion configuration, an initial deployed configuration and a review configuration in which the clip can be viewed prior to being finally deployed.

In particular, each of the extending members includes a hook at a distal end thereof configured to be looped over a portion of a corresponding one of the jaws to releasably couple the extending members to the clip so that the clip is movable relative to the endoscope between the insertion configuration, the initial deployed configuration and review configuration via the extending members. In the insertion configuration, the clip is mounted over the adapter in a proximal position maintained in the insertion configuration ready to receive tissue between jaws thereof while the clip's position minimizes its occlusion of the field of view of the endoscopic vision system. The insertion configuration is configured to facilitate insertion of the endoscope to a target site adjacent to tissue to be clipped while the system allows the clip to be deployed and clipped over tissue in an initial deployed configuration. The device permits the endoscope to be withdrawn proximally away from the clip and the tissue over which it is clipped while the clip remains coupled to the device in a review configuration.

As the endoscope is withdrawn proximally while the clip remains in place over the target tissue, the field of view of the vision system of the endoscope widens to show the clip and the tissue clipped thereby so that the operator can determine whether the position of the clip is desirable or in need of adjustment. If the operator determines that the clip is positioned as desired, the clip is deployed by releasing the clip from the hooked distal ends of the extending members and left in place clipped over the target tissue. If the operator determines that the position of the clip needs adjustment, the endoscope and the adapter coupled thereto are moved distally to a position adjacent to the clip. The clip is then drawn proximally over the adapter to reopen the clip which is drawn proximally over the distal end of the adapter forcing the clip to open against its natural bias as the clip slides proximally back over the adapter toward the insertion configuration.

After the clip has been removed from the tissue and returned to the insertion configuration, the operator can re-position the endoscope and device as desired, draw target tissue into the adapter (e.g., under suction or a grasper applied via a working channel of the endoscope) and once more deploy the clip from the adapter over the target tissue in the initial deployed position. The endoscope is then withdrawn proximally once again as the clip remains coupled to the device so that the device moves again into the review configuration. The position of the clip and the clipped tissue are again observed and, this process may be repeated until the clip is positioned as desired. When the operator sees that the tissue over which the clip is closed is the desired portion of tissue, the clip may be deployed and released from the device and endoscope as described below. It will be understood by those of skill in the art that terms proximal and distal, as used herein, are intended to refer to a direction toward and away from, respectively, a user of the device.

As shown in FIGS. 1-7, a clipping system 100 for treating tissue defects and/or perforations according to an exemplary embodiment comprises a clip 102 configured to be inserted through, for example, a body lumen to a target area to clip a target tissue thereof. The clip 102 is insertable to the target area via an insertion device 104 including, for example, an endoscope 106. The clip 102 is mountable to a distal end 108 of the endoscope 106 via an adapter 110 mounted to a distal end 108 of an endoscope 106 and is movable relative to the endoscope 106 via extending members 112, to which the clip 102 is releasably coupled.

Each of the extending members 112 includes a hook-shaped distal end 116 configured to be releasably looped over a portion of a corresponding jaw 114 of the clip 102 to facilitate movement of the clip 102 relative to the endoscope 106 between an insertion configuration, an initial deployed configuration, a review configuration, and a final deployed configuration. In the insertion configuration, the clip 102 is mounted over the adapter 110 with jaws 114 separated from one another to receive tissue therebetween. To move the clip 102 from the insertion configuration toward the initial deployed configuration, the extending members 112 are moved distally relative to the endoscope 106, permitting the clip 102 to be moved distally off the adapter 110 toward a closed configuration in which the jaw 114 are moved toward one another to grip tissue that has been drawn into the adapter 110.

Upon clipping of the tissue via the jaws 114 in the initial deployed configuration, the clip 102 may be moved toward the review configuration by moving the extending members 112 distally away from the endoscope 106 (or drawing the endoscope 106 proximally relative to the extending members 112) so that the clip 102 is distanced from the adapter 110, while remaining tethered to the insertion device 104 via the extending members 112. This widens the field of view of the endoscope vision system relative to the clip 102 and the target tissue and allows for some movement of the endoscope 106 relative to the clip 102 to enable more extensive observation of the placement and/or position of the clip 102 relative to the target tissue.

As described below, if the user determines the position of the clip 102 is incorrect or sub-optimal, the user may move the endoscope 106 distally to a position adjacent to the clip 102 and then retract the clip 102 proximally by withdrawing the extending members 112 proximally relative to the adapter 110 so that the clip 102 is drawn back over the distal end of the adapter 108 forcing the clip 102 open as it is slid proximally back over the adapter 110 to return to the insertion configuration. The user may then reposition the endoscope 106 and the clip 102 and repeat these steps so that the placement and/or position of the clip 102 relative to a target tissue may be adjusted prior to a final deployment of the clip 102. That is, if the operator sees in the review configuration that the clip 102 is not positioned as desired, the clip 102 may be re-opened and removed from the tissue so that the device can be re-positioned until the clip 102 is closed over the desired portion of tissue.

Once it is determined that the clip 102 has been clipped over the desired tissue, the extending members 112 are moved distally relative to the clip 102 so that the hook-shaped distal ends 116 disengage from the corresponding portions of the jaws 114, thereby separating the clip 102 from the insertion device 104 and deploying the clip 102 in the body. Although not shown, it will be understood by those of skill in the art that the movement of the clip 102 between the insertion configuration, the initial deployed configuration, the review configuration and the final deployed configuration may be controlled via a user interface which, in one embodiment, is coupled to a proximal end of the endoscope 106 and, in particular, includes an actuator coupled to proximal ends of the extending members 112 to impart proximal and distal movement to the proximal ends of the extending members 112 to achieve the desired corresponding movements of the distal ends of the extending members 112 as would be understood by those skilled in the art. Those skilled in the art will understand that although two extending members 112 are shown in this embodiment, any desired number of extending members 112 may be employed without departing from the scope of the disclosed embodiments.

As discussed above, the insertion device 104, as shown in FIG. 1, may include, for example, any standard endoscope 106. The clip 102 may be mounted to the endoscope 106 via the adapter 110 sized, shaped and configured to be mounted over the distal end 108 of the endoscope 106. As will be understood by those of skill in the art, the endoscope 106 is configured to be inserted through a body lumen to a target area within the lumen and thus, must be sufficiently flexible to navigate through even tortuous paths of the body lumen.

The adapter 110 extends from a proximal end 140 configured to be mounted to the distal end 108 of the endoscope 106 to a distal end 142 and includes a channel 144 extending therethrough. The adapter 110 may be mounted to the endoscope 106 via, for example, a friction fit, so that the channel 144 is substantially longitudinally aligned with a channel 146 of the endoscope 106. Thus, tissue is viewable through the channel 146 via an optical system of the endoscope 106. In another embodiment, the adapter 110 may also be formed of a transparent material to enhance the visibility of the tissue.

In one embodiment, the adapter 110 includes a pair of holes 130 extending longitudinally therethrough a wall thereof. The holes 130 are configured to slidably receive the extending members 112 therethrough. An outer diameter of the adapter 110 is sized, shaped and configured to receive the clip 102 thereover, in the insertion configuration. In one exemplary embodiment, the adapter 110 tapers from the proximal end 140 toward the distal end 142 so that the clip 102 is biased toward the initial deployed configuration.

The clip 102, however, may remain mounted over the adapter 110 in the open insertion configuration, with the jaws 114 separated from one another, so long as a sufficient proximally directed tension is applied to the extending members 112 so that the extending member 112 hold the clip 102 in place. If this tension is removed from the extending members 112, a natural bias of the clip 102 draws the jaws 114 toward one another pushing the clip 102 distally over the tapered surface of the adapter 110 until the clip 102 slides distally off of the adapter 110 as the extending members 112 are moved distally with the clip 102.

The insertion device 104, in one embodiment, includes a pair of extending members 112, each extending member 112 extending longitudinally along or within the endoscope 106 and the adapter 110 so that the extending members 112 are longitudinally movable relative to the endoscope 106. In one embodiment, each of the extending members 112 is independently movable relative to the other(s). In another embodiment, the extending members 112 may be move simultaneously relative to the endoscope 106. Each of the extending members 112 extend from a proximal end accessible to the user via, for example, an actuator, to the hook-shaped distal end 116, which extends distally of the endoscope 106 to be coupled to the clip 102.

As described above, the extending members 112 may extend through and/or along the endoscope 106 to be received within the holes 130 of the adapter 110 so that the distal ends 106 extend distally from the holes 130 to engage the clip 102. The extending members 112 may be moved longitudinally relative to the endoscope 106 to move the clip 102, which is coupled thereto, toward and away from the distal end 108 of the endoscope 106 between the insertion configuration, the initial deployed configuration and the review configuration.

According to an exemplary embodiment, each of the hook-shaped distal ends 116 extends along a J-shaped curve 138. In particular, each of the hook-shaped distal ends 116 extends along the curve 138 so that a hook tip 132 thereof extends in a proximal direction (e.g., toward the proximal end of the extending member 112). Thus, as will be described in further detail below, when the hook-shaped distal ends 116 are looped through corresponding portions of the clip 102, and tension is maintained along the extending members 112 relative to the clip 102, the distal ends 116 remain engaged with the clip 102.

Figure 4:
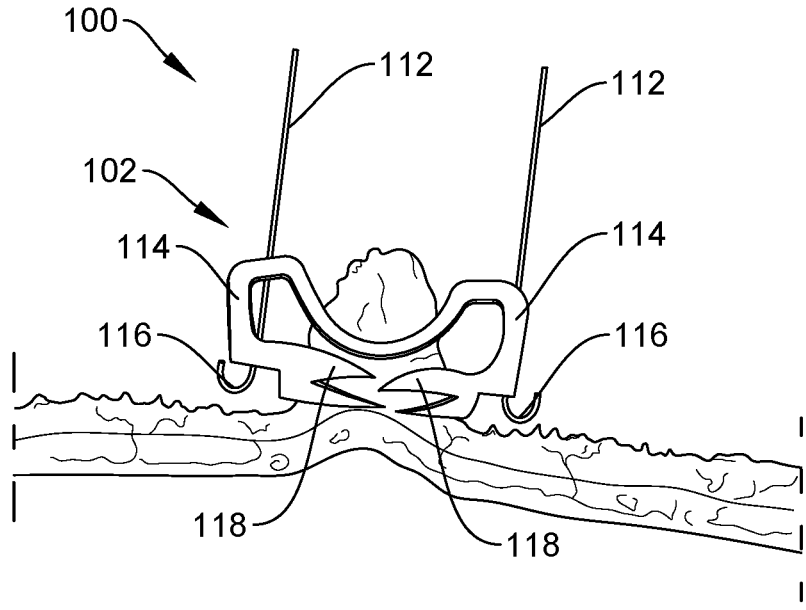
FIG. 4 shows a side view of the clip according to the system of FIG. 1, in a review configuration.

In one embodiment, the distal ends 116 of the extending members 112 are biased toward or away from one another, depending on a configuration of each of the extending members 112. For example, when the distal tips 132 are positioned in a radially outward position relative to a remaining longitudinal length (e.g., a portion of the extending members 112 extending along a length of the endoscope 106) of the extending members 112, as shown in FIGS. 1 and 4, the distal ends 116 may be biased toward one another.

If, however, the distal tips 132 are positioned in a radially inward position relative to the remaining longitudinal length of the extending members 112, the distal ends 116 may be biased away from one another. In either case, when the hook-shaped distal ends 116 are coupled to the clip 102, however, the distal ends 116 are constrained toward an engaged configuration. As will be described in further detail below, each of the distal ends 116 is looped over a portion of a corresponding one of the jaws 114 of the clip 102 so that the extending members 112 remain engaged with the clip 102 until it is desired to release the clip 102 in the final deployed configuration. Once the clip 102 has been clipped over a target tissue and moved toward the review configuration, however, moving the extending members 112 distally relative to the clip 102, causes the distal ends 116 to disengage from the clip 102 so that the distal ends 116 are permitted to revert to their biased configuration, in which the distal ends 116 move radially inward or outward relative to one another. Thus, since the distal ends 116 are moved out of engagement with the clip 102, the insertion device 104 may be drawn proximally away from the clip 102 and removed from the body so that just the clip 102 remains deployed in the body.

In another embodiment, however, the distal ends 116 are not required to be biased relative to one another. Rather, to disengage the clip 102 from the distal ends 116 of the extending members 112 toward the final deployed configuration, as will be described in further detail below, each of the extending members 112 is moved independently relative to the others and longitudinally relative to the clip 102 so that when the distal end 108 of the endoscope 106 is moved laterally to correspondingly move a desired one of the extending member 112 out of engagement with the clip 102.

Figure 2:
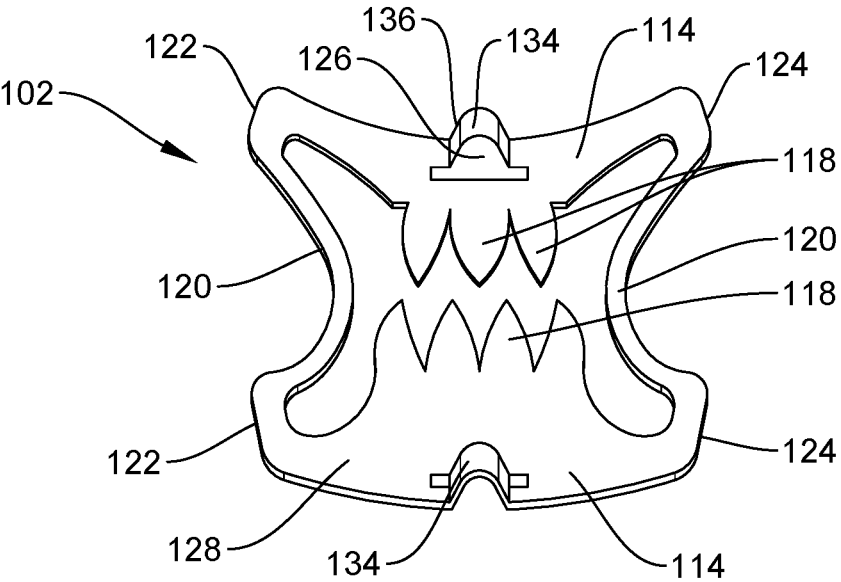
FIG. 2 shows a perspective view of a clip according to the system of FIG. 1.
Figure 3:
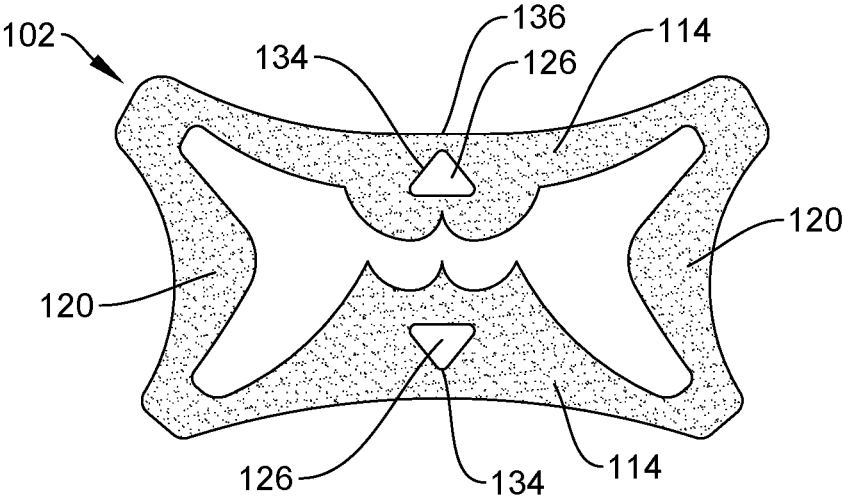
FIG. 3 shows a plan view of the clip according to the system of FIG. 1.

As shown in FIGS. 2-3, the clip 102 includes a pair of jaws 114 and, in this embodiment, each of the jaws 114 includes gripping features 118 such as, for example, teeth, for gripping target tissue. The jaws 114 of the clip 102 of this embodiment are connected to one another via hinges 120. In one embodiment, each of the jaws 114 extends along a curve from a first end 122 to a second end 124 so that a first one of the hinges 120 connects the first ends 122 of each of the jaws 114 to one another, while a second one of the hinges 120 connects the second ends 124 of each of the jaws 114 to one another.

In one embodiment, the hinges 120 are spring biased, biasing the jaws 114 toward the initial deployed configuration in which the jaws 114 are closed so that the gripping features 118 of one of the jaws 114 contact tissue located therebetween. In particular, in the initial deployed configuration, the jaws 118 extend toward one another so that target tissue may be gripped between the jaws 114 via, for example, the gripping features 118. However, when the clip 102 is mounted over the adapter 110 in the insertion configuration, the jaws 114 are stretched over opposing portions of the adapter 110 so that an exterior surface of the adapter 110 maintains the clip 102 open with the jaws 114 separated from one another so that the target tissue drawn into the adapter 110 is positioned therebetween.

When the clip 102 is moved distally off the adapter 110, the clip 102 is freed to close under the natural bias of the hinges 120. It will be understood by those of skill in the art that the hinges 120 and/or jaws 114 of the clips 102 may be formed of any of a variety of materials so long as the hinges 120 bias the jaws 114 toward the initial deployed configuration, as described above and so that the bias is sufficiently strong to maintain the clip 102 in position clipped over target tissue after the clip has been finally deployed. In one example, portions of the clip 102 (e.g., the hinges 120) are formed of a shape memory alloy such as, for example, Nitinol to provide and/or add to the bias toward the closed configuration.

In one embodiment, each of the jaws 114 also includes a slot 126 via which the extending members 112 releasably engage the clip 102. The slot 126 of this embodiment extend through each of the jaws 114, midway between the first and second ends 122, 124 thereof. The slot 126 may be sized and shaped to receive a hook tip 132 of each of the hook-shaped distal ends 116. In particular, the hook tip 132 may be received within the slot 126 so that an engaging section 134, which is defined via a portion of the slot 126 and an exterior edge 136 of each of the jaws 114 (i.e., an edge along a portion of the jaw 114 opposing the gipping features 118), is received within the curve 138 of the hook-shaped distal end 116 of each of the extending members 112. In other words, the hook-shaped distal end 116 is looped over the engaging section 134 to be releasably coupled to the clip 102.

According to an exemplary embodiment, the engaging section 134 may also be defined via a stiff, raised portion of the jaw 114 so that when the extending members 112 are engaged with the clip 102, the distal ends 116 are not pushed against tissue gripped via the clip 102, as shown in FIG. 4. In other words, the engaging section 134 protrudes away from a surface 128 of the clip 102 which, when the clip 102 is gripped over tissue, extends away from the tissue. Thus, there is sufficient room for the distal ends 116 to be moved out of engagement with the clip 102 when it is desired to disengage the clip 102 from the extending members 112, toward the final deployed configuration.

As shown in FIGS. 5-6, so that the distal ends 116 of the extending members 112 may engage and disengage the clip 102 as desired, an interior width A1 of the curve 138 (e.g., a diameter of the curve 138) of each of the distal ends 116 should be greater than a width A2 of the engaging section 134 (e.g., a distance between the exterior edge 136 of the jaw 114 and an edge 148 of the slot 126 closest thereto). In addition, an overall width B1 of the distal end 116 should be less than a width B2 of the slot 126. The width B2 of the slot 126 may defined as a distance between the edge 148 and a portion of an opposing edge 150 that is farthest away from of the edge 148. It will be understood by those of skill in the art that the slot 126 and a cross-section of the distal ends 116 of the extending members 112 may have any of a variety of shapes and sizes so long as the distal ends 116 are configured to be hooked through the slots 126 of the jaws 114 and engaged/disengaged therewith, as described above.

According to an exemplary method for tissue closure utilizing the clipping system 100, the clip 102 is inserted through a body lumen such as, for example, the GI tract, to a target area within the body lumen via an insertion device 104 (for example, an endoscope 106). As described above, in the insertion configuration, the clip 102 is mounted to the distal end 108 of the endoscope 106 via the adapter 110, so that the jaws 114 are separated from one another in the open configuration. The clip 102 is guided to the target area via the visualization system of the endoscope and positioned over a target tissue. A grasping device or suction force is then applied through a working channel of the endoscope 104 so that the target tissue is drawn into the channel 144 of the adapter 110. Thus, when the clip 102 is moved toward the initial deployed configuration by releasing a tension along the extending members 112 (e.g., moving the extending members 112 proximally relative to the endoscope 106), the clip 102 slides distally along the adapter 110 toward the biased closed configuration to grip the target tissue.

It will be understood by those of skill in the art that suctioning and/or gripping of the tissue in this initial deployed configuration may obstruct an imaging/optical lens of the endoscope 106 so that the user is unable to visualize and/or confirm whether a desired target tissue has been properly clipped. Thus, the clip 102 may be moved toward the review configuration by drawing the endoscope 106 distally relative to the clip 102, while the clip 102 remained clipped on the tissue. A distance between the adapter 110 and the clip 102 widens a field of view of the endoscope 106 so that the clip 102, and the tissue gripped thereby, may be viewed via the optical/visualization system of the endoscope 106.

If, upon visualization, the user determines that the clip 102 requires an adjustment and/or a repositioning relative to the target tissue, the extending members 112 may be translated proximally relative to the endoscope 106 until the clip 102 is moved proximally over the adapter 110, as described above, toward the open configuration. As the clip 102 is moved toward the open configuration, the tissue gripped thereby is released, permitting the clip 102 to be repositioned over the target tissue, as desired. The clip 102 may then once again moved toward the initial deployed configuration, and then toward the review configuration. This process may be repeated, as necessary, until the user is able to visually confirm that the clip 102 has been clipped over the target tissue, as desired.

Once the user confirms that the target tissue has been clipped, as desired, the clip 102 may be moved from the review configuration to the final deployed configuration, by releasing the clip 102 from the extending members 112. As described above, in one embodiment, the extending members 102 may be moved distally relative to the clip 102. As the extending members 112 are moved distally relative to the clip 102, the hook-shaped distal ends 116 disengage the engaging sections 134 of the clip 102. As the distal ends 116 are released, the distal ends 116 are oved toward their biased configuration, radially toward or away from one another depending on an orientation of each of the distal ends 116 relative to the clip 102.

For example, where the curves 138 of the hook-shaped distal ends 116 curve radially outwardly to engage the clip 102, as shown in the FIG. 4, the distal ends 116 may be biased radially inwardly relative to one another. Where the curves 138 of the hook-shaped distal ends 116 curve radially inwardly to engage the clip 102, the distal ends 116 may be biased radially outwardly relative to one another. Thus, movement of the extending members 112 distally of the clip 102, moves the distal ends 116 out of engagement with the clip 102 so that the distal ends 116, allowing the distal ends to revert toward their biased configuration so that the extending members 112, and the remaining portions of the insertion device 104, may be moved proximally away from the clip 102 and withdrawn from the body.

In another embodiment in which the distal ends 116 are not biased relative to one another, the extending members 112 are moved independently relative to one another. For example, when it is desired to move the clip 102 from the review configuration to the final deployed configuration, a first one of the extending members 112 is moved distally relative to the clip 102 so that the distal end 116 thereof is disengaged from a corresponding one of the engaging sections 134. The distal end 108 of the endoscope 106 is then moved laterally relative to a longitudinal axis of the insertion device 104 so that the first extending member 112 is correspondingly moved relative to the clip 102. The distal end 108 of the endoscope 106 is moved until the distal end 106 is aligned with a corresponding one of the slots 126 so that the distal end 116 is removable therefrom by drawing the first extending member 112 proximally relative to the clip 102.

Upon removal of the first extending member 112 from the clip 102, a second one of the extending members 112 may be similarly moved distally relative to the clip 102 until the distal end 116 thereof disengages a corresponding one of the engaging sections 134 of the clip 102. The distal end 108 of the endoscope 106 is then moved in a lateral direction relative to the longitudinal axis of the insertion device 104 until the distal end 116 of the second extending member 112 is aligned with a corresponding one of the slots 126 so that drawing the second extending member 112 proximally relative thereto removes the distal end 116 of the second extending member 112 therefrom. Thus, the extending members 112 are separated from the clip 102 and the insertion device 104 may be removed from the body so that just the clip 102 remains in the body, clipped over the target tissue, in the final deployed configuration.

Although the clip 102 of the system 100 is shown and described as including the slots 126 and the engaging sections 134 for engaging the hook-shaped distal ends 116 of the extending members 112, it will be understood by those of skill in the art that the clip 102 may have any of a variety of engaging features configured to similarly engage the hook-shaped distal ends 116 of the insertion device 104. The engaging features of the clip 102 may have any of a variety of configurations so long as the hook-shaped distal ends 116 may be hooked or looped to a corresponding portion of the jaws 114 to engage the clip 102 so that the clip 102 is movable between the insertion, initial deployed, review and final deployed configurations, as described above.

Figure 8:
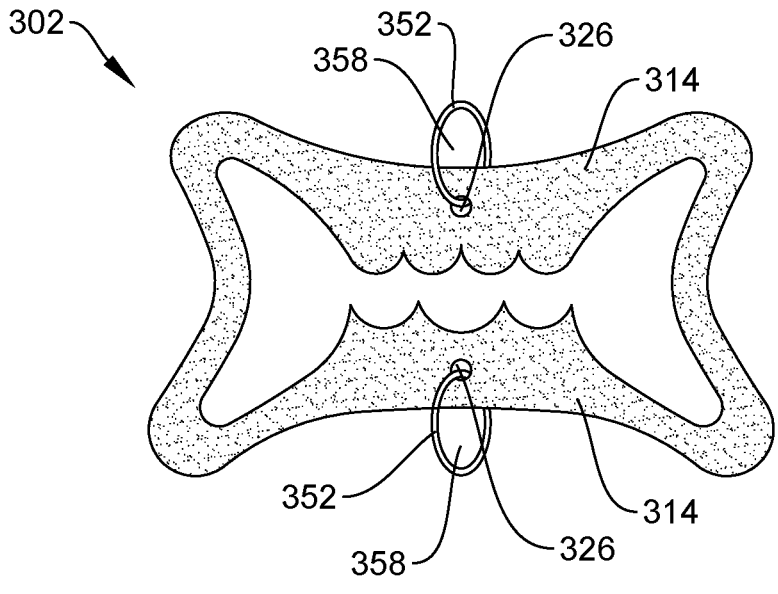
FIG. 8 shows a plan view of a clip according to another exemplary embodiment of the present disclosure.
Figure 9:
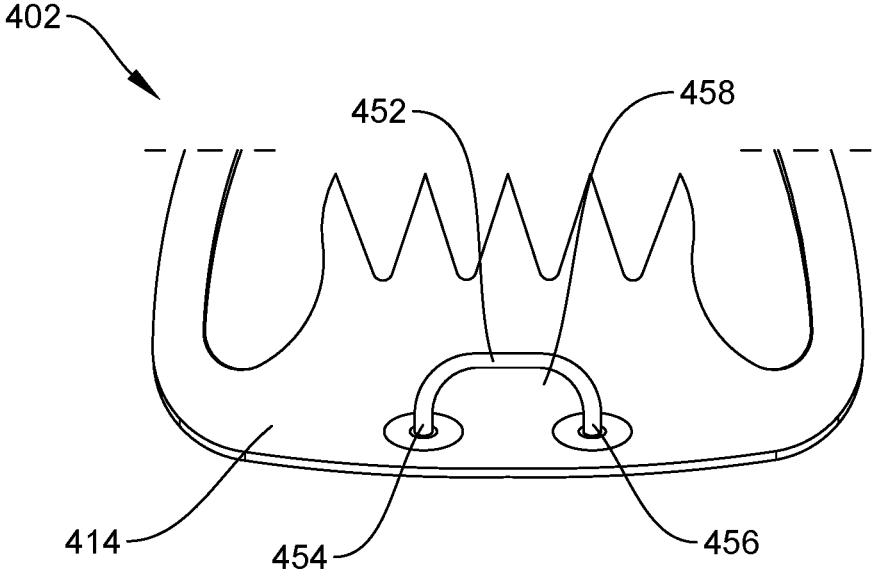
FIG. 9 shows a partial plan view of a clip according to yet another exemplary embodiment of the present disclosure.

In one exemplary embodiment, as shown in FIG. 7, rather than a slot, each jaw 214 of a clip 202 may include a wire 252 extending from a first end 254 attached to the jaw 214 to a second end 256 including a loop 258 sized, shaped and configured to engage a corresponding one of the hook-shaped distal ends 116. In another exemplary embodiment, as shown in FIG. 8, each jaw 314 of a clip 302 may include a hole 326 extending therethrough. A wire 352 is looped through each hole 326 to form a closed loop 358 that is configured to be engaged via a corresponding one of the hook-shaped distal ends 116. In yet another embodiment, as shown in FIG. 9, each jaw 414 of a clip 402 may include a wire 452 attached to thereto to form a loop 458 configured to be engaged via a corresponding one of the hook-shaped distal ends 116. First and second ends 454, 456 of the wire 452 are attached to a surface of the jaw 414 to form the loop 458.

Figure 10:
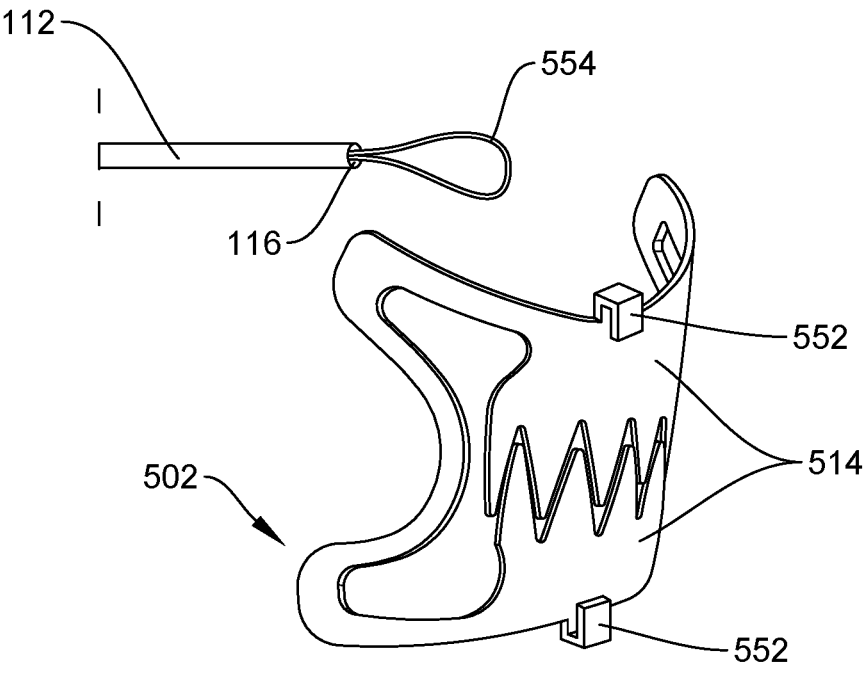
FIG. 10 shows a perspective view of a clip according to another exemplary embodiment.

In a further exemplary embodiment, as shown in FIG. 10, rather than a slot, each jaw 514 of a clip 502 includes a hook 552 extending from each of the jaws 514. In this embodiment, each of the extending members 112 includes a snare 554 extending from its distal end 116. The hook 552 is sized, shaped and configured to engage the snare 554. In the insertion configuration, the extending members 112 are positioned so that the snare 554 is looped around the hook 552. As the extending members 112 are extended distally to move the clip 502 off of the adapter 110, the snare 552 remains looped over the hook 552.

When the clip 502 leaves the adapter 110 and clips over tissue, the user may move the clip to the final deployed configuration by manipulating the extending members 112 to remove the snares 552 from the hooks 552 (e.g., by moving the loops of the snares 554 off of the free ends of the hooks 552). If the user wishes to reposition the clip 502 after the snares 554 have been removed from the hooks 552, the extending members 112 may be manipulated to loop the snares 554 back over the hooks 552. The user may then pull the extending members 112 proximally to draw the clip 502 back over and onto the adapter 110 as described above in regard to the previous embodiments.

Figure 11:
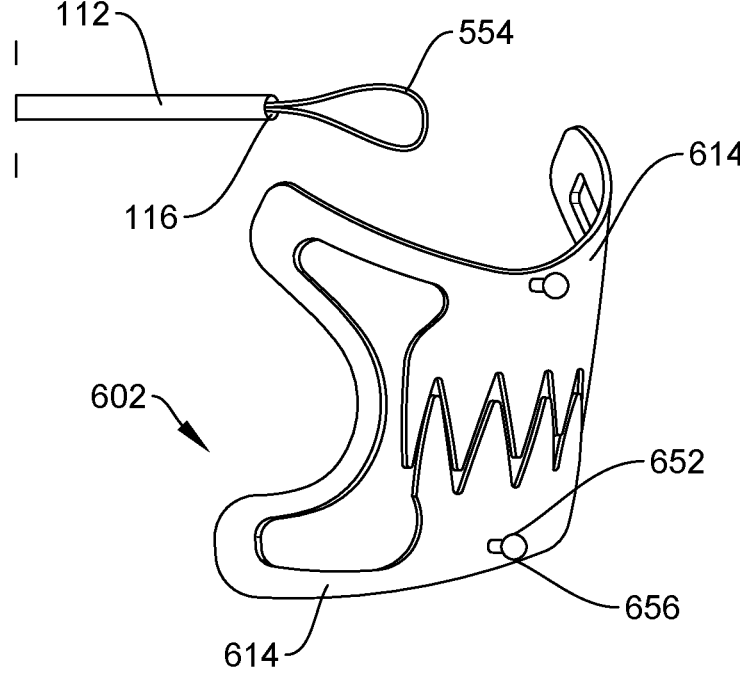
FIG. 11 shows a perspective view of a clip according to a further exemplary embodiment.

In another exemplary embodiment, as shown in FIG. 11, each jaw 614 of a clip 602 includes a post 652 extending distally from each of the jaws 614 to an enlarged head 656. The post 652 is sized, shaped and configured to engage the snare 554. Similar to the clip 502, in the insertion configuration, the extending members 112 are positioned so that the snare 554 is looped around the post 652 with the enlarged head 656 assisting in maintaining the snare 554 looped around the post 652 as the clip 602 is moved between the insertion, initial deployed and review configurations. As the extending members 112 are extended distally to move the clip 602 off of the adapter 110, the snare 554 remains looped over the post 652. When the clip 602 leaves the adapter 110 and clips over tissue, the user may move the clip 602 to the final deployed configuration by manipulating the extending members 112 to remove the snares 554 from the post 652 (e.g., by moving the loop of the snare 552 over the enlarged head 656 and off of the free end of the post 652). If the user wishes to reposition the clip 602 after the snares 654 have been removed from the posts 652, the extending members 112 may be manipulated to loop the snares 554 back over the posts 652. The user may then pull the extending members 112 proximally to draw the clip 602 back over and onto the adapter 110 as described above in regard to the previous embodiments.

It will be understood by those of skill in the art that the clips 202-602, as described above, may be utilized with the insertion device 104, in a manner substantially similar to the method, as described above with respect to system 100. In particular, upon engagement of the extending members 112 to the clips 202-402, the clips 202-402 may be moved between the insertion, initial deployed, review and final deployed configuration via movement of the extending members 112 longitudinally relative to the endoscope 106, as described above.

It will be apparent to those skilled in the art that various modifications may be made in the present disclosure, without departing from the scope of the disclosure. Furthermore, those skilled in the art will understand that the features of any of the various embodiments may be combined in any manner that is not inconsistent with the description and/or the functionality of the embodiments.

What is claimed is:

1. A clipping system for treating tissue, comprising:
an adapter extending longitudinally from a proximal end to a distal end, the adapter configured to be mounted over a distal end of a longitudinally extending insertion device that is configured to be inserted through a body lumen to a target area within the body lumen;
a clip configured to be mounted over the adapter, the clip including first and second jaws connected to one another so that the first and second jaws are movable between an insertion configuration, in which the first and second jaws extend over opposing portions of the adapter so that an exterior surface of the adapter separates the first and second jaws from one another to receive tissue therebetween, and an initial deployed configuration, in which the clip is moved distally off of the adapter so that the first and second jaws are drawn toward one another to grip tissue therebetween, the clip being biased toward the initial deployed configuration, the first jaw including a first jaw connector; and a first extender configured to be releasably coupled to the clip, the first extender extending longitudinally from a proximal end accessible to a user at a proximal end of the insertion device to a distal end including a first releasable connector configured to be releasably coupled to the first jaw connector, the first extender being configured to permit movement of the adapter relative to the clip while the first extender remains coupled to the clip to place the system in a review configuration in which the clip is physically spaced from the adapter to enhance visual observation of the clip, the first extender being operable to retract the clip proximally over the adapter so that the clip is forced open as the clip is retracted over the adapter freeing the clip from tissue on which it had been clipped.

2. The system of claim 1, wherein the first jaw connector includes a slot extending through the first jaw and wherein the first releasable connector includes a hook, the slot being sized and shaped to releasably receive the hook.

3. The system of claim 2, wherein a width of the slot is smaller than a diameter of a curvature of the hook.

4. The system of claim 2, wherein a width the slot is larger than a width of the distal end of the first extender so that the distal end of the first extender is releasable from the first jaw connector.

5. The system of claim 1, wherein the first jaw connector includes a wire extending from the first jaw and wherein the first releasable connector includes a hook-shaped curvature at the distal end of the first extender, the wire including a loop configured to engage the hook-shaped curvature of the first extender.

6. The system of claim 5, wherein a first end of the wire is attached to the first jaw and a second end of the wire includes the loop sized, shaped and configured to be hooked via the distal end of the first extender.

7. The system of claim 5, wherein the wire is looped through a hole extending through the first jaw to form a closed loop configured to be hooked via the distal end of the first extender.

8. The system of claim 5, wherein the wire extends from a first end to a second end, each of the first and second ends attached to a surface of the first jaw so that the wire defines a loop configured to be hooked via the hook-shaped curvature of the first extender.

9. The system of claim 1, further comprising a second extender configured to be releasably coupled to a second jaw connector of the second jaw, a distal end of the second extender including a hook-shaped curvature configured to engage the second jaw connector.

10. A clipping system for treating tissue, comprising:

an endoscope extending longitudinally from a proximal end to a distal end;

an adapter extending longitudinally from a proximal end configured to be mounted over the distal end of the endoscope so that a channel of the adapter is aligned with a channel of the endoscope;

a clip configured to be mounted over the adapter, the clip including first and second jaws connected to one another so that the first and second jaws are movable between an insertion configuration, in which the first and second jaws extend over opposing portions of the adapter so that the first and second jaws are separated from one another via an exterior surface of the adapter to receive tissue therebetween, and an initial deployed configuration, in which the clip is slid distally off of the adapter so that the first and second jaws are drawn toward one another to grip tissue therebetween, the clip being biased toward the initial deployed configuration, each of the first jaw including a first jaw connector; and first and second extenders configured to be releasably coupled to the clip and movably connected to the adapter, the first and second extenders extending longitudinally from a proximal end accessible to a user at the proximal end of the endoscope to a distal end, the distal end of the first extender including a first releasable connector configured to be releasably connected to the first jaw connector so that longitudinal movement of the first extender relative to the endoscope moves the clip between the insertion configuration, the initial deployed configuration and a review configuration in which the clip is physically separated from the adapter to enhance visual observation of the clip, a proximal movement of the first extender relative to the adapter configured to retract the clip proximally over the adapter toward the insertion configuration to release tissue gripped between the first and second jaws.

11. The system of claim 10, wherein the first jaw connector includes a slot extending through the first jaw and wherein the first releasable connector includes a hook-shaped curvature at the distal end of the first extender, the slot defining an engaging section of the first jaw between the slot and an exterior edge of the first jaw, the engaging section configured to be received within the hook-shaped curvature of the first extender.

12. The system of claim 11, wherein the first jaw includes a wire coupled thereto, the wire including a loop configured to engage the hook-shaped curvature of the first extender.

13. The system of claim 12, wherein a first end of the wire is attached to the first jaw and a second end of the wire includes the loop that is sized, shaped and configured to be hooked via the distal end of the first extender.

14. The system of claim 12, wherein the wire extends from a first end to a second end, each of the first and second ends being attached to a surface of the first jaw so that the wire defines a loop configured to be hooked via the hook-shaped curvature of the first extender.

* * * * *